United States Patent [19]
Morrison

[11] Patent Number: 5,947,891
[45] Date of Patent: Sep. 7, 1999

[54] METHOD AND APPARATUS FOR HOMOGENEOUSLY IRRADIATING THE VAGINAL MUCOSA WITH A LINEAR SOURCE UTEROVAGINAL APPLICATOR

[76] Inventor: Richard A. Morrison, 9021 Delmar, Shawnee Mission, Kans. 66207

[21] Appl. No.: 08/843,092

[22] Filed: Apr. 25, 1997

[51] Int. Cl.[6] .................................................. A61N 5/00
[52] U.S. Cl. ................................................................. 600/6
[58] Field of Search ........................ 600/1–8; 604/51–53, 604/55, 93, 117, 171

[56] References Cited

U.S. PATENT DOCUMENTS

| | | | |
|---|---|---|---|
| 4,244,357 | 1/1981 | Morrison | 600/6 |
| 4,331,131 | 5/1982 | Kumar | 600/6 |
| 4,434,789 | 3/1984 | Kumar | 600/6 |
| 4,554,909 | 11/1985 | Torres | 600/6 |

*Primary Examiner*—Samuel Gilbert
*Attorney, Agent, or Firm*—Hovey, Williams, Timmons & Collins

[57] ABSTRACT

A therapeutic instrument for irradiative treatment of the genital tract is provided comprising a tubular applicator, a separable vaginal retainer and an interlocking structure between the two. The tandem is adapted to receive a linear tube containing multiple sources of radiant energy and terminates at its inner end in a curved intrauterine portion. Two halves of the separable retainer surround the tandem and cooperatively form a vaginal cylinder for occupying the vaginal vault and a handle. The interlocking structure includes outwardly extending projections and cavities in the handle so positioned that the structure is visible to the physician at all times.

19 Claims, 2 Drawing Sheets

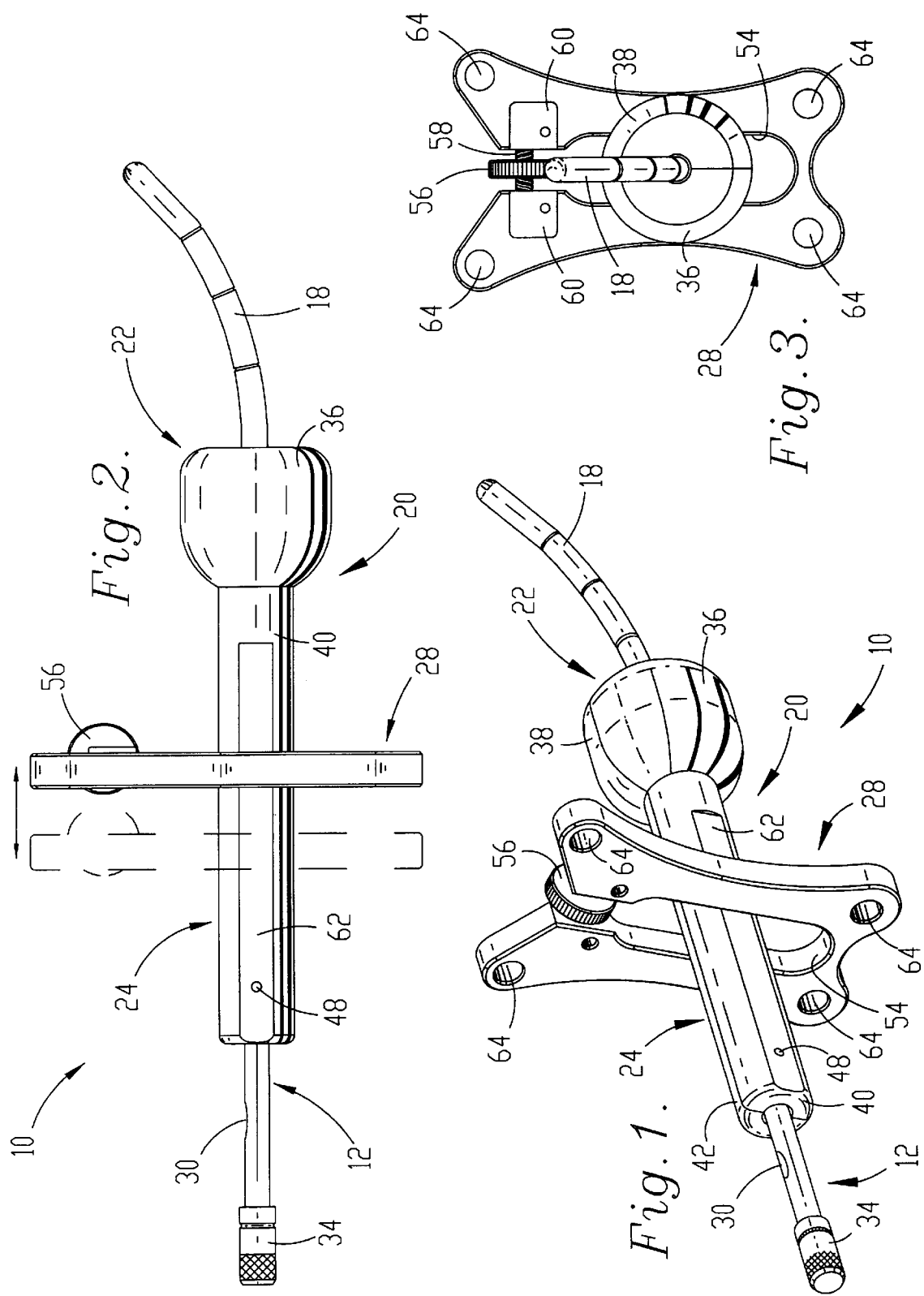

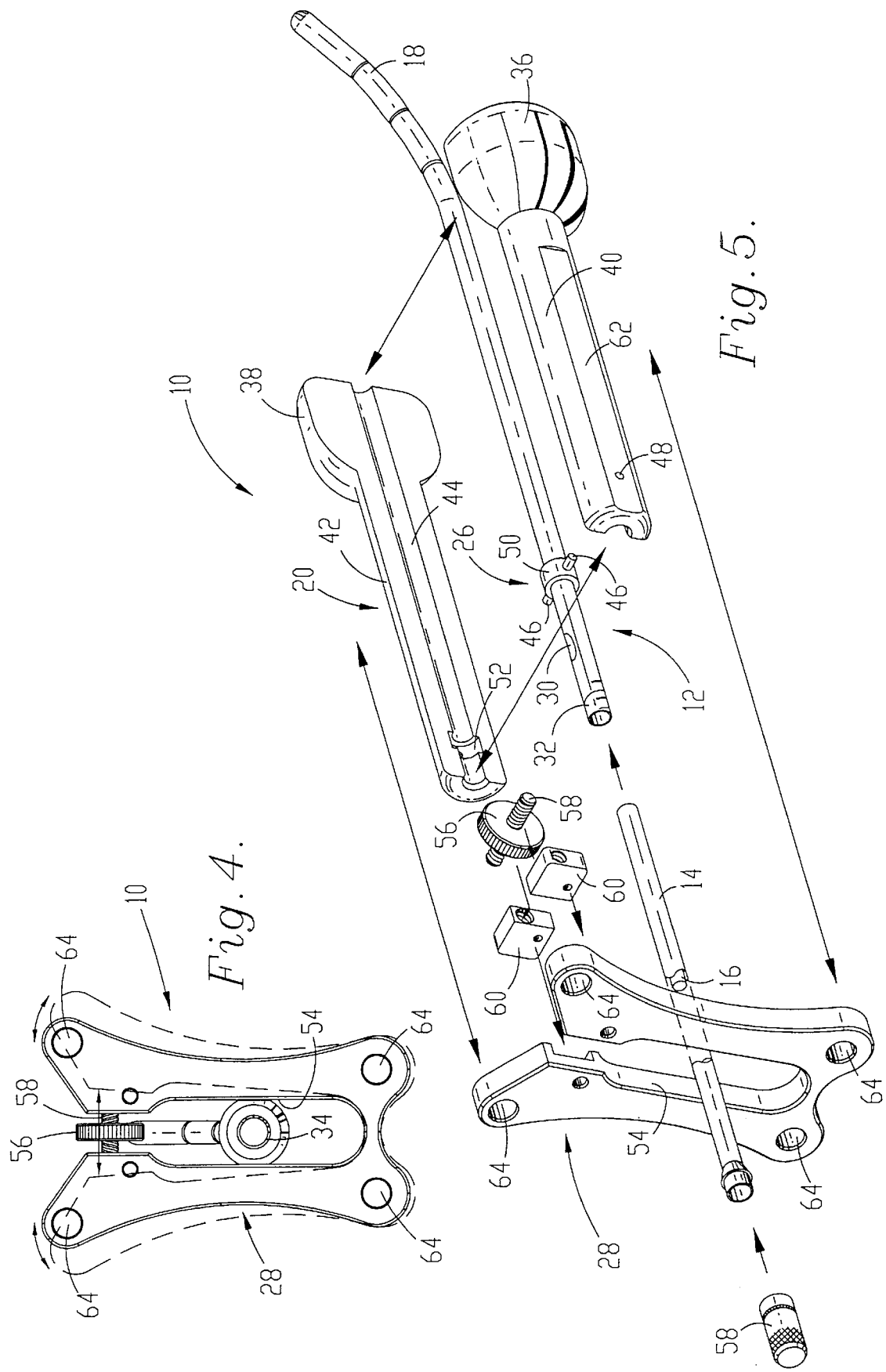

METHOD AND APPARATUS FOR HOMOGENEOUSLY IRRADIATING THE VAGINAL MUCOSA WITH A LINEAR SOURCE UTEROVAGINAL APPLICATOR

BACKGROUND OF THE INVENTION

1. Field of the Invention

The present invention relates to a uterovaginal tool for treating cancer of the uterine cervix and, more particularly, to such a tool having a slender tube first inserted into the vagina followed by an easily attached vaginal retainer to keep the tube correctly positioned within the uterus.

2. Discussion of the Prior Art

Radiotherapy is and has been the treatment of choice in the management of invasive cancer of the uterine cervix for many years. A high percentage of cases can be cured when the disease is limited to the uterus and vagina. The risk of a tumor recurrence or therapeutic complication depends primarily on the ability of the radiotherapist to produce a dose distribution which eradicates the tumor and yet does not exceed normal tissue tolerances.

In some instances, linear source uterovaginal applicators are used in preference to nonlinear source applicators and have the following advantages:

A. Simpler and easier afterloading with radioactive sources;

B. Dose homogeneity around the entire circumference of the vaginal vault; and

C. Greater flexibility in fitting different anatomical sizes and disease distributions.

One of the basic principles of radiation treatment with a cylindrical applicator having a central linear source is to employ the greatest treatment distance (cylinder radius) which the patient's anatomy will permit. In this way, there is not such a precipitous fall in dose below the surface and the effective thickness of tissue which can be adequately irradiated is maximal.

Conventional linear source uterovaginal applicators are in the form of one-piece cylinders of varying lengths and diameters which slip over a tube (tandem) containing the central linear source and passing through the vagina into the uterine cavity. The diameter of the vaginal cylinder which may be used is limited by the size the vaginal introitus, which in most instances is less than that of the vaginal vault.

My prior U. S. Pat. 4,244,357 discloses a linear source uterovaginal applicator which has proven to be a good tool for the treatment of uterine cancer but was found to have some shortcomings. That patent described a tube (tandem) insertable through the vagina into the uterine cavity and a retainer for the tandem comprising two half cylinders (bivoids) for occupying the vaginal cavity. The bivoids were individually insertable through the vaginal introitus. Upon assembly they would be held together by the vagina walls and cooperate to hold the tandem in place by an interlocking device. Having individually insertable bivoids allowed the physician to use a vaginal cylinder (two bivoids) of a diameter limited only by the size of the vaginal cavity—not the vaginal introitus.

However, the interlocking structure is located within the bivoids, and because the bivoids become enveloped within the vaginal cavity during use, the physician is unable to see if the bivoids are properly locked to the tandem. Furthermore, my earlier invention included an apparatus for inserting the bivoids which contained many separate parts. Consequently, additional time and effort was needed to attach the handles to and disconnect them from the bivoids.

OBJECTS AND SUMMARY OF THE INVENTION

Accordingly, one important object of the present invention is to provide a uterovaginal applicator which utilizes the desirable concept of separately insertable bivoids of my previous invention but is easier to use and provides the physician with more certainty that the intrauterine portion of the tandem is properly positioned and securely held in place.

This objective is achieved in the present invention by simplifying the apparatus used to insert the bivoids into the vagina. By integrating the bivoids with a handle, I am able to move the interlocking device from within the bivoids and inside the vagina, to a position on the handle outside the vagina where the locking means is accessible and visible at all times to the physician.

My improved uterovaginal applicator uses two bivoids which are each integral with their own handle. Each handle is used to insert its respective bivoid through the vaginal introitus. Once assembled around the tandem, an intravaginal retainer is formed with one vaginal cylinder and one handle.

Additionally, my improved applicator includes an exposed interlocking device located near the outermost end of the tandem and which retains the handles against axial movement on the tandem. The device further maintains the position of the intrauterine applicator relative to the bivoids for the maximum dose distribution to the uterine cervix.

Moreover, the rigid tandem of my applicator is held within the intravaginal retainer which is fixed securely to a clamp overlying the perineum. The clamp is fastened with gauze straps to an elastic bandage around the patient's waist. In this manner, the intrauterine portion of the tandem is held midway between the bladder anteriorly and the rectosigmoid posteriorly and overdosage of these structures is avoided.

BRIEF DESCRIPTION OF THE DRAWING FIGURES

A preferred embodiment of the invention is described in detail below with reference to the attached drawing figures, wherein:

FIG. 1 is a perspective view of my fully assembled, improved uterovaginal applicator with the tandem locked within the intravaginal retainer;

FIG. 2 is right side-elevational view showing the adjustable retainer clamp and its direction of travel;

FIG. 3 is an interior end-elevational view of the applicator;

FIG. 4 is an exterior end-elevational view of the applicator illustrating the clamping motion of the retainer clamp; and FIG. 5 is an exploded perspective view showing the components of my improved uterovaginal applicator, including the tandem, the two halves of the intravaginal retainer, the tandem clamp and its components.

DETAILED DESCRIPTION OF THE PREFERRED EMBODIMENT

An assembled uterovaginal applicator 10 includes an elongated, tubular intravaginal tandem 1 2 that is adapted to receive a linear tube 14 as shown in FIG. 5 containing multiple sources of radiant energy, such as cesium tubes 16. The tandem 12 terminates at its inner end in a curved intrauterine portion 18. Two halves of a separable intravaginal retainer 20 surround the tandem 12 and cooperatively form a cylindrical intravaginal body 22 for occupying the vaginal cavity and an elongated handle 24 projecting axially away from the body 22. Structure broadly denoted by the number 26 (FIG. 5) releasably interlocks the tandem 12 and the assembled intravaginal retainer 20 to prevent axial movement of the tandem. A clamp 28 is mounted on the handle 24 to keep both halves of retainer 20 interlocked upon the tandem 12.

The tandem 12 and adjoining intrauterine portion 18 are preferable formed of stainless steel. The tandem is provided with a bevel 30 remote from outermost end of the handle 24 such that the bevel faces the direction of the upward curvature of the intrauterine portion 18. Screw threads 32 on the outermost end of the tandem 12 opposite to the portion 18 are adapted to receive a closure cap 34. The stainless steel closure cap is threaded upon the tandem 12 to prevent the linear tube 14 from sliding out of the tandem.

The separable intravaginal retainer 20 is preferable formed of a suitable synthetic resinous material. The halves of the cylindrical intravaginal body 22 include bivoids 36, 38 having a generally flat inner end and curved outer end. The halves of the handle 24 include handle portions 40, 42 for inserting their respective bivoids through the vaginal introitus. The assembled intravaginal retainer 20 forms a tandem receiving transversely circular bore 44 running the length of the retainer.

When the tandem 12 is housed within the bore 44 structure 26 interlocks the tandem and the intravaginal retainer 20. The structure 26 includes a pair of diametrically opposed, radially outwardly extending projections 46, preferably stainless steel pins, on the tandem 12 and pair of correspondingly positioned pin receiving cavities 48 in the handle portions 40, 42. The pins 46 are mounted on a stainless steel collar 50 coaxial with the tandem and attached rigidly to the same. The handle portions 40, 42 further include cavities 52 that matingly receive the collar 50 when the retainer 20 is surrounding the tandem 12.

In my prior applicator as disclosed in my '357 Patent, the structure which locks the tandem to the bivoids is so located that it becomes hidden from view when the physician inserts the tandem into the vagina. Consequently, as each bivoid is inserted along the tandem and into the vagina, it is difficult to see the interlocking structure retain each bivoid. The physician must assume the bivoids are properly locked to the tandem. If the tandem is not securely held by the bivoids and intrauterine portion moves away from the area which is being treated, the maximum dose distribution will not be achieved. To correct this problem, I permanently attached a handle to each bivoid allowing the interlocking structure to be moved outside the vagina. With the interlock in sight, the physician then has visual confirmation that the retainer is properly assembled and the tandem is locked within.

The clamp 28, formed of a suitable synthetic resinous material, has concave edges and V-shaped ends as seen in FIG. 1 with an intermediate, longitudinally extending, handle-receiving slot 54, terminating in a widened portion within which is disposed a knurled turnknob 56 affixed to a screw 58 having left and right-hand threads meshed with nuts 60 mounted on the clamp 28. The handle portions 40, 42 each present a flat surface 62 to which the clamp 42 can be drawn tight against precluding rotation about the handle and longitudinal displacement. Corner holes 64 in the clamp 28 are adapted to receive gauze straps (not shown) which are, in turn, adapted to be fastened to an elastic bandage (not shown) around the patient's waist.

TECHNIQUE OF APPLICATION

Following the administration of a general anesthetic, the patient is placed in the dorsal lithotomy position. The perineum and vagina are washed with antiseptic solution. If urinary retention is expected, an indwelling catheter may be inserted; however, in most instances it will not be necessary. In order to obtain a clearer view of the cervix and vaginal fornices, a triple-bladed speculum is employed. The cervical canal is searched for with a uterine sound. Occasionally, when the canal is not readily apparent, one must hold the cervix with a single-tooth tenaculum, but this should be avoided if possible. Once the cervical canal has been identified, the uterine cavity is sounded and the depth noted. The canal is then progressively dilated, and the appropriate length tandem 12 is inserted into the uterine cavity.

The size of the vaginal bivoids 36, 38 which can be accommodated is estimated by the displacement of the three blades of the speculum and a little experience. Always the largest diameter possible should be selected, and the length should be such that the lowermost extent of the vaginal tumor does not extend beyond the center of the lowermost vaginal source. Using the attached handle portion 40 bivoid 36 is inserted along the tandem 12 until the pin 46 and collar 50 are visually seen to be received into the opening 48 and cavity 52 within the handle portion 40. The bivoid 38 is then passed along the tandem 12 until the opposed pin 46 and collar 50 are visually seen to be received into the opening 48 and cavity 52 within the handle portion 42. A final look is taken to be sure the halves of the intravaginal retainer 20 are properly assembled on the tandem 12 and interlocked by structure 26, resulting in the correct positioning of the intrauterine applicator 18 adjacent the uterine cervix.

When short bivoids 36, 38 are required, a short length of antiseptic-impregnated gauze is wrapped around the exposed tandem 12. A suitable length of gauze is passed through each hole 64 of the clamp 28. The clamp 28 is placed loosely over the handle 24 of the intravaginal retainer 20. The patient's legs are then lowered slowly to the supine position on the operating table. The tandem 12 and the loosened clamp 28 are allowed to come to a natural, comfortable position, then the clamp screw 58 is tightened securely. The four ends of the gauze straps are fastened to an elastic bandage around the patient's waist to hold the clamp 28 in place exteriorly of the vagina orifice across the external genitalia between the urethra and anal orifices. The patient may now lie on her back or either side in comfort, and she may empty her bladder or bowel in bed without soilage. In route from the recovery room to the ward room, radiographs are obtained to check the position of the tandem 12.

The applicator loadings and treatment times for each of two subcourses are obtained from the table corresponding to the particular combination of tandem and bivoids used. The first subcourse loading of the tandem 12 is inserted in the afternoon and is replaced with the second subcourse loading the following morning. The next day, the tandem 12 is removed at the patient's bedside. An anelgesic is not required. The gauze straps are cut; then the clamp 28 is loosened and removed. The protruding end of the intravaginal retainer is separated releasing the handle portions 40, 42 from the interlocking device. The bivoids 36, 38 can then be individually removed from within the vaginal vault by manipulating their respective handles portions. Finally, the tandem 12 is removed with a curvilinear motion so that the cervix is not traumatized.

While cesium-137 is indicated as a source of radiation because it is in common use, my invention contemplates any radionuclide which spontaneously emits gamma rays including, but not limited to, cobalt-60 and radium-226. Readily available, however, are cesium-137 tubes constructed of two stainless steel capsules, including an inner core and an outer casing to insure the integrity of the source. Oftentimes, the source is loaded with thousands of cesium-labeled ceramic microspheres, resulting in a consistently uniform active length. Usually, each tube is engraved with a nominal activity and serial number, nickel-plated, and color-coded on the eyelet end of the source. The applicator 10 of my present invention, including the tandem 12 with its vaginal retainer 20 is especially adaptable for receiving various radiation therapy products such as cesium-137 brachytherapy sources.

The above-described method and apparatus for homogeneously irradiating the vaginal mucosa with a linear source uterovaginal applicator maintains the vaginal vault distended by virtue of the bivoids inserted with integral handles on the tandem 12 itself such that, as above indicated, the maximum distance available between the source and the vaginal mucosa is utilized to provide an improved percentage depth dose to the vagina, as distinguished from linear source applicators heretofore suggested and employed in the treatment of malignant tumors of the human female genital organs.

What is claimed is:

1. A therapeutic instrument for irradiative treatment of the genital tract by subjecting the genital tract to radiant energy, said instrument comprising:

an elongated, tubular, uterovaginal tandem having a nomally outermost end, and tandem terminating at a normally innermost end thereof in a tubular, intrauterine applicator, said tandem having an inlet at the normally outermost end adapting the tandem and the intrauterine applicator for afterloading with a linear source of radioactive energy having isodose curves in the form of concentric circles surrounding the tandem;

a retainer having an axial, Tandem receiving bore therethrough, said retainer comprising a cylindrical intravaginal body and an elongated handle projecting axially away from said body, said retainer being separable along an axis of the bore to present a pair of separately insertable intravaginal bivoids, each bivoid being provided with an individual handle portion to facilitate insertion of the bivoids into the vagina vault through the vaginal introitus and into place on the tandem after insertion of the tandem into said tract until the intrauterine applicator is disposed within the uterine cavity; and structured releasably interlocidng said handle and said tandem to preclude axial movement of the tandem when the tandem is received in said bore and the body of the retainer is disposed within the vagina vault.

2. The invention of claim 1, said structure including at least one projection and one receiving cavity for the projection.

3. The invention of claim 2, said projection being attached to said tandem, the receiving carity being formed in said handle for receiving said projection.

4. The invention of claim 3, said projection comprising a pair of opposed, radially outwardly extending pins secured to a collar coaxial with and fixed to said tandem, said receiving cavity having an opening for retaining said pins and collar.

5. The invention of claim 1, said structure being located between said bivoids and an outer must end of said handle and adapted to be exposed for visual identification outside said vaginal introitus.

6. The invention of claim 1, further including an elongated, perineal member slidable along the handle longitudinally thereof toward and away from the intravaginal bivoids, said member being provided with take-up means for clamping the same to the handle in any one of a number of preselected positions therealong.

7. The invention of claim 6, said member having a longitudinal slot, said handle being provided with a slot-receiving length having an irregular, transverse, external configuration for precluding rotation of the member around said length.

8. The invention of claim 1 further comprising a linear source of radioactive energy inserted in the tandem.

9. A therapeutic instrument for irradiative treatment of the genital tract by subjecting the same to radiant energy, said instrument comprising:

an elongated, tubular, uterovaginal tandem having a normally outermost end, and the tandem terminating at a normally innermost end thereof in a tubular, intrauterine applicator, said tandem having an inlet at the normally outermost end adapting the tandem and the intrauterine applicator for afterloading with a linear source of radioactive energy having isodose curves in the form of concentic circles surrounding the tandem;

a retainer having an axial, tandem receiving bore therethrough, said retainer comprising a cylindrical intravaginal body and an elongated handle projecting axially away from said body, said retainer being separable along an axis of the bore to present a pair of separately insertable intravaginal bivoids, each bivoid being integral with an individual corresponding handle portion to facilitate of the bivoids into the vagina vault through the vaginal introitus and into place on the tandem after insertion of the tandem into said tract until the intrauterine applicator is disposed within the uterine cavity.

10. The invention of claim 9, including structure releasably interlocking said handle and said tandem to preclude axial movement of the tandem when the tandem is received in said bore and the body of the retainer is disposed within the vagina vault.

11. The invention of claim 10, further including a projection being attached to said tandem, there being a receiving cavity formed in said handle for receiving said projection.

12. The invention of claim 11, said projection comprising a pair of opposed, radially outwardly extending pins secured to a collar coaxial and fixed to said tandem, said receiving cavity retaining said pins and collar.

13. The invention of claim 9, further including an elongated, perineal member slidable along the tandem longitudinally thereof toward and away from the intravaginal bivoids, said bivoids being disposed between the intrauterine applicator and said member, said member being provided with take-up means for clamping the member to the tandem in any one of a number of preselected positions therealong.

14. The invention of claim 13, said member having a longitudinal slot, said handle being provided with a slot-receiving length having an irregular, transverse, external configuration for precluding rotation of the member around said length.

15. The invention of claim 13, and clamping the member to the tandem after the member is in engagement with the perineum.

16. The invention of claim 10, said structure being located between said bivoid and an outermost end of said handle and adapted to be externally exposed for visual identification outside of said vaginal introitus.

17. The invention of claim 16, and sliding a retention member along the tandem into engagement with the perineum.

18. The invention of claim 9 further comprising a linear source of radioactive energy inserted in the tandem.

19. A method of irradiative treatment of the genital tract by subjecting the genital tract to radiant energy, said method including the steps of:

inserting an elongated, tubular, uterovaginal tandem into the tract through the vaginal introitus and thence through the cervical canal until a portion of a length of the tandem is disposed within the uterine cavity;

inserting a separable retainer having a pair of initially separate intravaginal bivoids providing handle portions into said tract until the intravaginal bivoid is in complete surrounding relationship to the tandem within the vaginal vault adjacent the cervix, by using the handle portions to separately and successively slide the bivoids along the tandem, locking said handle portions to said tandem at a position exteriorly of the vaginal intrious; and loading the tandem with a linear source of radioactive energy having isodose curves in the form of concentric circles, whereby the maximum distance between said source and the vaginal mucosa is utilized to thereby provide for equal, regular and uniform, maximum percentage dose delivery of radiant energy to the entire circumference of the vagina.

* * * * *